(12) United States Patent
Bradshaw

(10) Patent No.: US 6,976,972 B2
(45) Date of Patent: Dec. 20, 2005

(54) SUSPENSION WALKER

(75) Inventor: Jason L Bradshaw, Eaton, CO (US)

(73) Assignee: Scott Orthotic Labs, Inc., Fort Collins, CO (US)

( * ) Notice: Subject to any disclaimer, the term of this patent is extended or adjusted under 35 U.S.C. 154(b) by 63 days.

(21) Appl. No.: 10/658,069

(22) Filed: Sep. 9, 2003

(65) Prior Publication Data

US 2005/0054962 A1    Mar. 10, 2005

(51) Int. Cl.⁷ .............................................. A61F 5/00
(52) U.S. Cl. ........................ 602/23; 602/27; 602/28; 602/12; 128/882; 36/140; 36/159
(58) Field of Search ........................ 602/12, 23, 27–30, 602/60, 65–66, 5; 128/869, 882; 2/22; 36/88–89, 36/91, 93, 15, 140, 145, 150, 155, 159–160, 36/164–165

(56) References Cited

U.S. PATENT DOCUMENTS

| | | | | |
|---|---|---|---|---|
| 3,827,431 A | * | 8/1974 | Pecorella .................... | 602/16 |
| 4,517,968 A | * | 5/1985 | Greene et al. ................ | 602/27 |
| 5,078,128 A | | 1/1992 | Grim et al. | |
| 5,138,774 A | * | 8/1992 | Sarkozi ....................... | 36/164 |
| 5,197,942 A | | 3/1993 | Brady | |
| 5,306,230 A | * | 4/1994 | Bodine ........................ | 602/26 |
| 5,317,820 A | * | 6/1994 | Bell et al. .................... | 36/89 |
| 5,329,705 A | | 7/1994 | Grim et al. | |
| 5,368,551 A | * | 11/1994 | Zuckerman .................. | 602/23 |
| 5,429,588 A | | 7/1995 | Young et al. | |
| 5,464,385 A | | 11/1995 | Grim | |
| 5,571,078 A | * | 11/1996 | Malewicz .................... | 602/27 |
| 5,577,998 A | | 11/1996 | Johnson, Jr. et al. | |
| 5,620,411 A | | 4/1997 | Schumann et al. | |
| 5,761,834 A | | 6/1998 | Grim et al. | |
| 5,827,210 A | | 10/1998 | Antar et al. | |
| 5,833,639 A | | 11/1998 | Nunes et al. | |
| 5,971,946 A | * | 10/1999 | Quinn et al. ................. | 602/27 |
| 5,993,404 A | * | 11/1999 | Mc Niel ...................... | 602/23 |
| 6,024,713 A | | 2/2000 | Barney | |
| 6,228,044 B1 | | 5/2001 | Jensen et al. | |
| 6,267,742 B1 | * | 7/2001 | Krivosha et al. ............. | 602/28 |
| 6,443,919 B1 | | 9/2002 | Castro | |
| 6,464,659 B1 | | 10/2002 | DeToro et al. | |
| 2002/0128574 A1 | * | 9/2002 | Darby ......................... | 602/23 |
| 2002/0138030 A1 | | 9/2002 | Cavanagh et al. | |

OTHER PUBLICATIONS

Bledsoe Conformer Brochure, 2001.
Bledsoe Conformer Brochure, Jun. 2002.
DONJOY Brochure.
Paper by J. Martin Carlson, 1992.
Scott Orthotic Labs, Inc. Brochure.

* cited by examiner

Primary Examiner—Henry Bennett
Assistant Examiner—Amanda Wieker
(74) Attorney, Agent, or Firm—W. Scott Carson

(57) ABSTRACT

A suspension walker having a hard, outer boot shell with upright brace members attached on either side and a soft boot receivable thereon. The soft boot has a main pad in it with a removable, fitting pad or pads on top of the main pad. A cuff member is also provided that is securable to the patient's calf and to the upright brace members. In use, the fitting pad is removed during the initial fitting and subsequent uses to suspend the patient's foot in the walker. The cuff member is also infinitely adjustable along the brace members to vary the fit as desired.

43 Claims, 14 Drawing Sheets

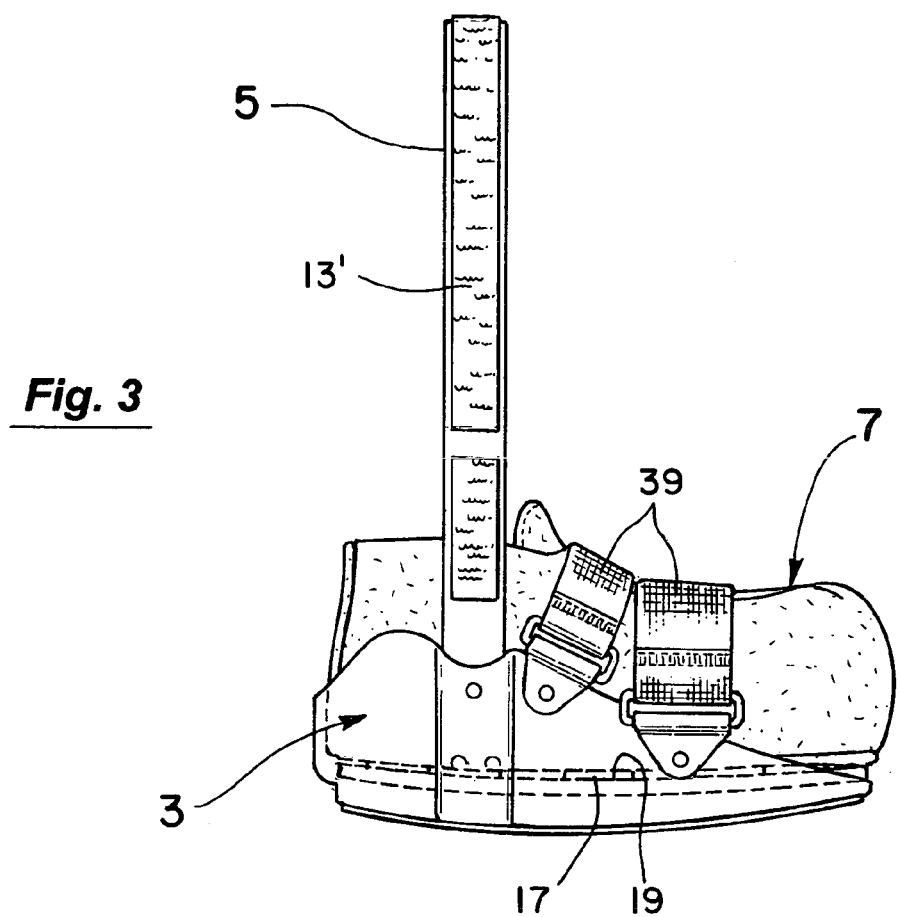
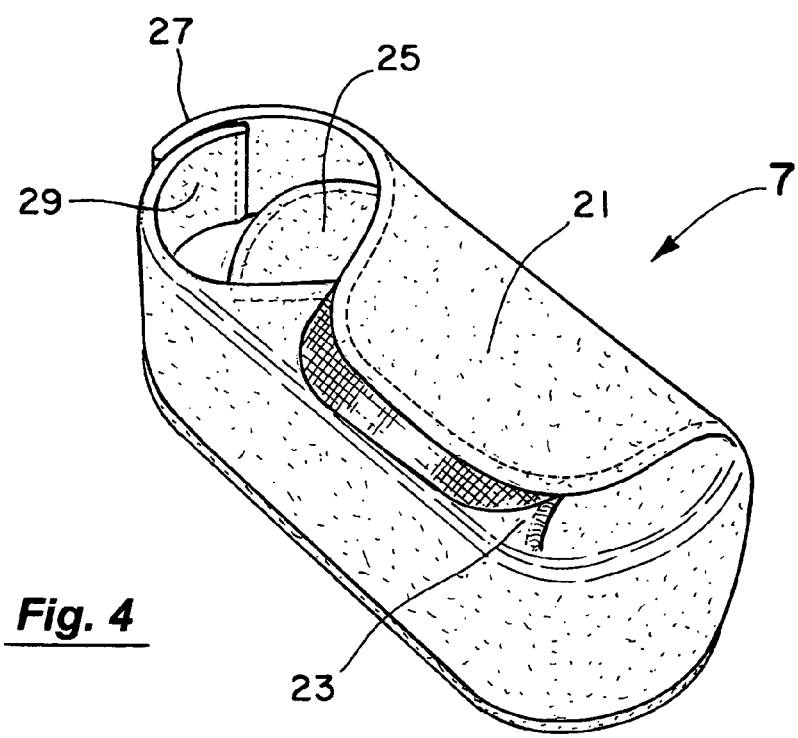

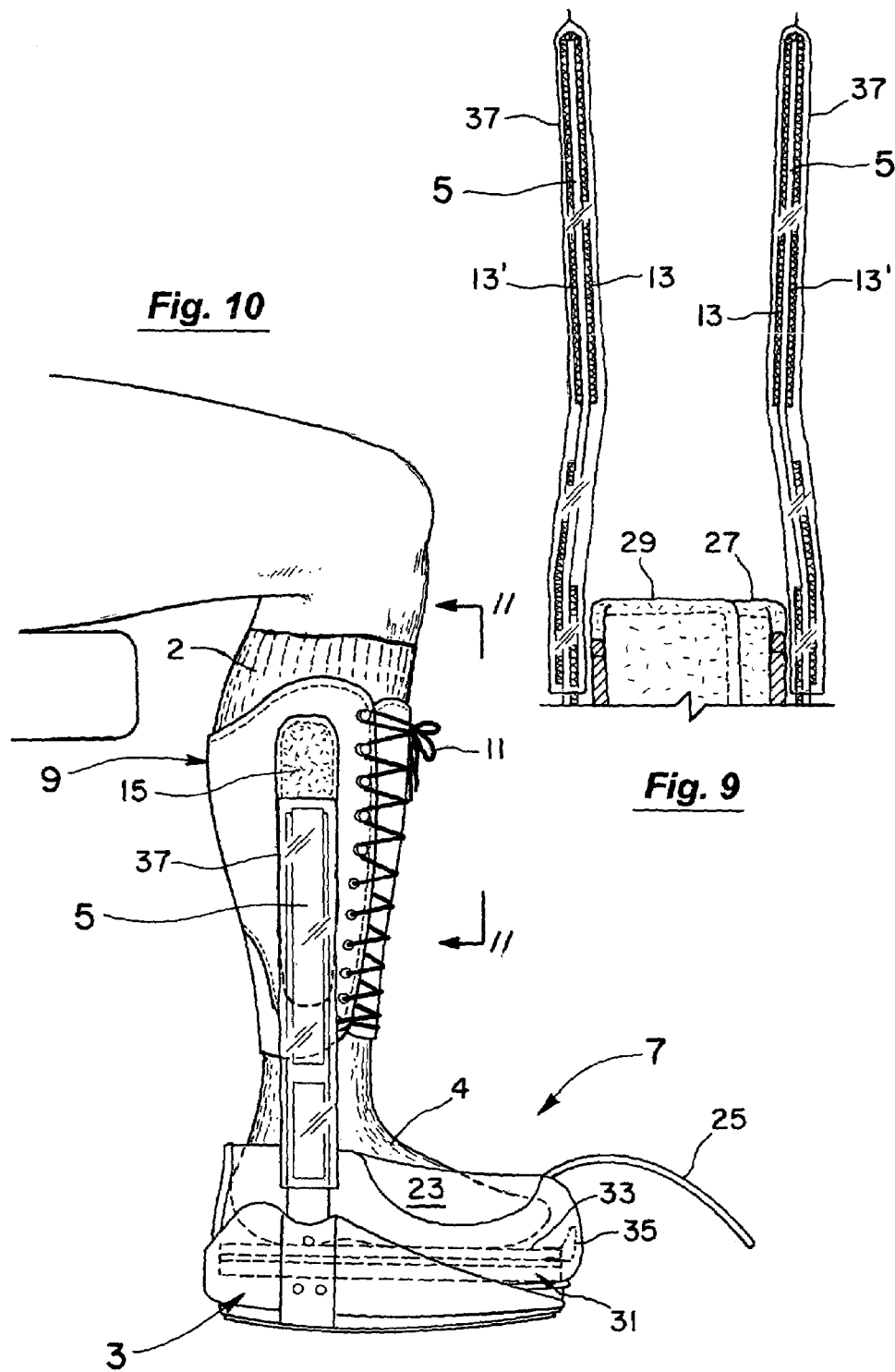

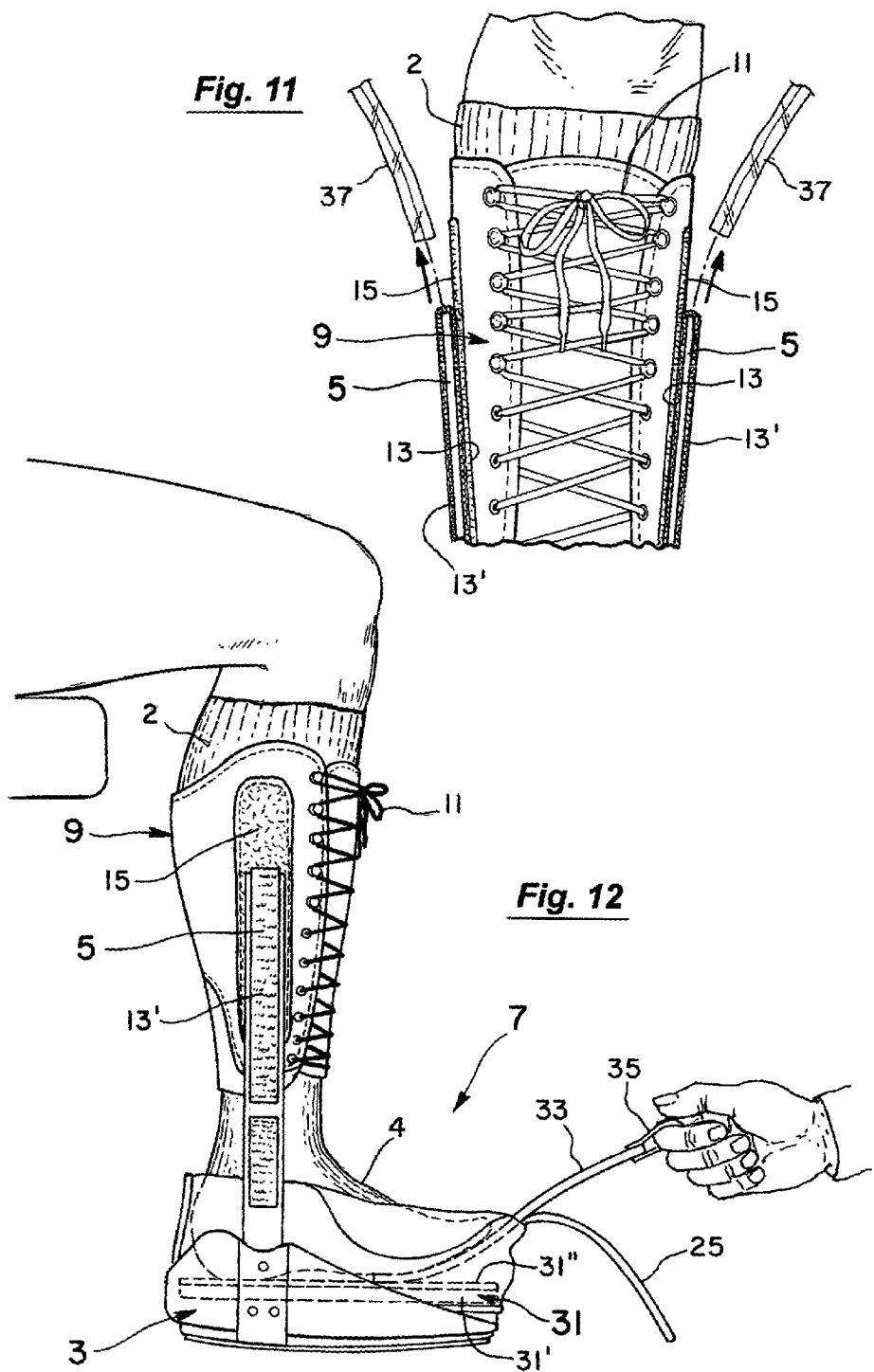

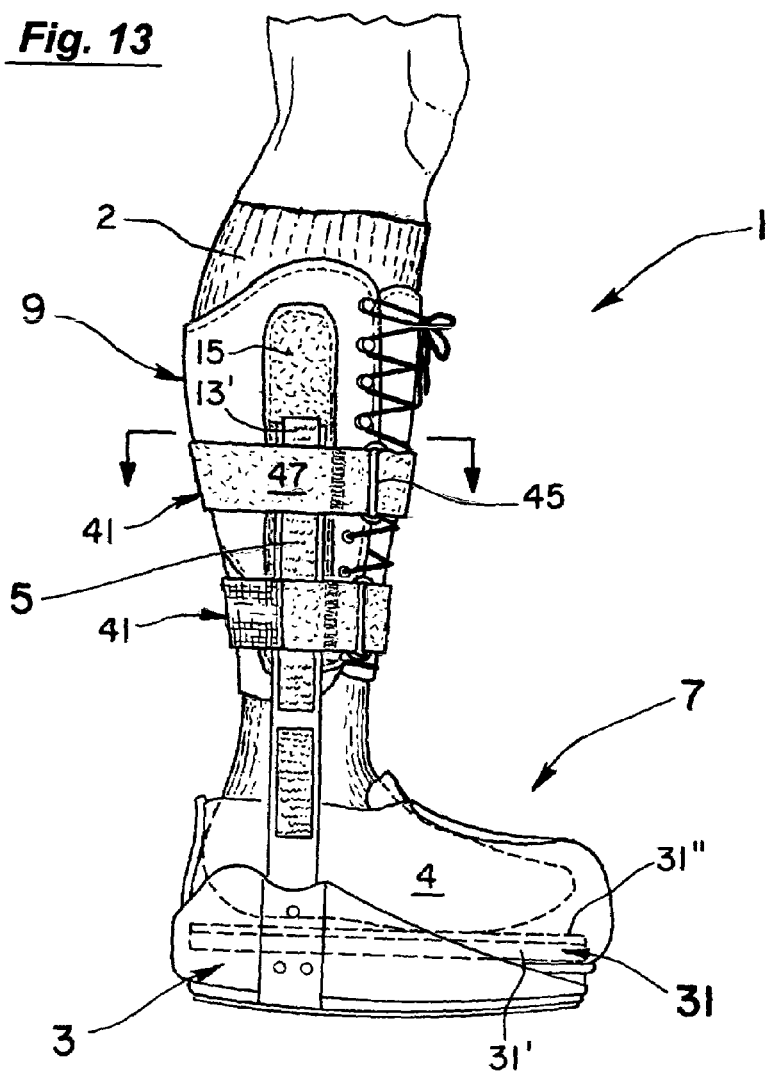
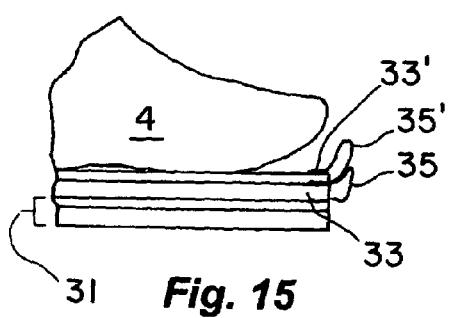
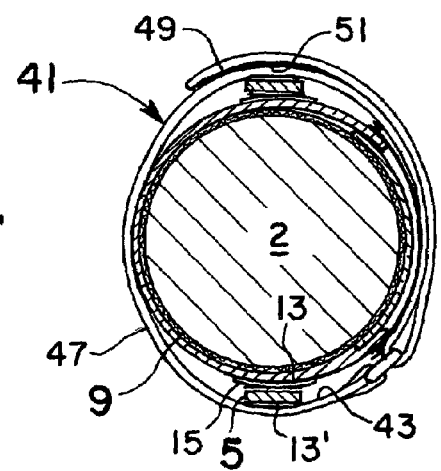

SUSPENSION WALKER

BACKGROUND OF THE INVENTION

1. Field of the Invention

This invention relates to the field of suspension walkers and more particularly to the field of such walkers that transfer weight normally borne by the patient's foot to his or her calf.

2. Discussion of the Background

Many people and diabetics in particular develop sores or ulcers on the soles of their feet. To heal, they must either stay off their feet altogether or use a pressure relieving orthosis or brace. Generally, these orthoses are of two designs.

In the first design as typified by U.S. Pat. No. 5,761,834 to Grim, the orthosis is provided with adjustable pads (see its FIGS. 7–12) in which the contour and/or density of the pad sections is modified. In the modification of FIG. 8 of this patent, for example, a piece of a sectionalized pad is removed at 186 in an effort to relieve pressure on the area of the sore. This first approach has not met with great success as the gap (in the case of FIG. 8 of this patent) or the contour/density changes of the other figures of this patent tend to present their own pressure or rubbing points and may make new sores or make the existing sore worse. The removed section in particular often creates a suction on the sore as the patient walks that aggravates it in addition to the sides of the gap rubbing on the area around the sore creating new sores.

In a second design commonly known as custom suspension walkers, the concept is to transfer some of the weight normally borne by the foot to the patient's calf. In doing so, a leather or similar wrap or cuff fits around the calf of the patient wherein the cuff is secured to the patient's calf and to upright braces extending downwardly to a hard boot or shoe. In use, a large portion (e.g., 50%) of the patient's weight is then transferred to his calf and off of his foot. In essence, the patient's foot is suspended at least to the extent of the weight borne by the calf via the cuff and braces extending downwardly to the shoe.

In one prior technique for making a suspension walker, a negative cast of the patient's foot is first taken. The cast is then cut down the front so the patient can remove his foot and the cut cast is sent to a custom manufacturer. The manufacturer can subsequently follow one of many procedures to make a custom walker. In one procedure, a positive cast is made from the hollow, negative cast and a leather cuff is sweated (tightly fitted) about the calf area. The cuff is then mounted on the vertical braces at a height slightly greater (e.g., ½ inch) than the true position of the original cast. In use, the person puts his calf in the cuff and laces it up. In doing so, the cuff fits the calf but since the cuff has been raised on the braces, the effect is that the foot is slightly suspended in the shoe with the calf via the cuff and braces now bearing some of the patient's weight.

In another procedure, the negative cast is cut below where the cuff would be and a spacer inserted to in essence raise the normal position of the calf and cuff. The leather cuff is then sweated (fitted) to the calf of the positive cast but unlike the first procedure, the cuff can be attached to the brace members at the same level as the cast and does not need to be raised. Because the positive cast has the calf area slightly higher than normal, the end result is thus the same as in the first procedure (i.e., weight is transferred to the calf and the foot is suspended).

Current suspension walkers and the fitting techniques discussed above are very effective; however, they have two, primary drawbacks. First and foremost is the time. That is, the injured patient normally needs a walker at the same time (i.e., immediately) he complains of or is diagnosed with the sore. However, the custom manufacture and the fitting procedures mentioned above normally take days and often weeks. The patient also usually needs to make a follow-up visit to the doctor or manufacturer to make sure the fit is correct and he knows how to use the walker. Second, custom walkers are relatively expensive as they are very labor intensive at the manufacturer level and as previously indicated normally require multiple fitting trips to the physician, practitioner, or therapist in addition to the original casting person.

With the above in mind, the present invention was developed. With it, a suspension walker is provided that can be immediately fitted to the patient in the office of the physician, practitioner, or therapist. The walker avoids the need for taking castings and the custom work mentioned above. It can also be made available in prefabricated sizes and for less expense as there is very little labor involved in fitting the walker to the patient and training the patient in its proper use.

SUMMARY OF THE INVENTION

This invention involves a suspension walker. The walker includes a hard, outer boot shell with upright brace members attached on either side. A soft boot is received in the shell and has a main pad in it with a removable, fitting pad or pads on top of the main pad. The soft boot has a tongue and two side flaps that open up to expose the inside of the soft boot and to receive the patient's foot. A cuff member is also provided that is securable to the patient's calf and to the upright brace members.

To fit the patient, the cuff member is attached comfortably about the patient's calf and then the patient puts his foot into the open boot. Normally, the patient is sitting down as he puts his foot into the boot atop the main pad and the removable, fitting pad. Up to this point, the upright brace members preferably have plastic covers over them. In this regard, the cuff member has one portion of hook and loop or VELCRO® fasteners on each outer side. Additionally, the brace members have the other portions of hook and loop fasteners on their respective insides. In this way and with the patient's foot in a fitted position in the soft boot, the plastic covers can be removed from the brace members wherein the cuff member will be secured to the brace members at the desired position via the hook and loop fasteners.

The fitting pad can then be manually removed and the tongue and side flaps of the soft boot closed with the result that the foot is at least partially suspended via the cuff and brace members on the main pad. In a typical procedure, the fitting pad may be ½ inch thick for the fitting step wherein 50% or so of the patient's weight is transferred off the foot to the calf and via the cuff and brace members to the hard, outer boot shell.

With this new design, the suspension walker is immediately available for use by the patient to begin healing the sore. Additionally, the physician, practitioner, or therapist can easily and quickly set the proper or desired degree of weight suspension by using different thicknesses of the removable, fitting pad or pads (e.g., ¼ or ½ inch pad or the two together to equal a ¾ inch pad). This is done at the first office visit with immediate feedback from the patient on how it feels versus the often imprecision and follow-up fittings nearly always needed with present custom walkers, which have many steps done without the patient present.

Another fundamental advantage of the present design is that the patient on subsequent days can then duplicate the fitting originally done by the physician, practitioner, or therapist. In doing so, the patiently only has to re-insert the fitting pad(s) into the soft boot with the cuff member already attached in the desired position to the brace members by the hook and loop fasteners. The cuff member can subsequently be laced up with the patient's foot in the soft boot followed by the removal of the fitting pad(s). In contrast, the prior walkers required some experimentation and mental input by the patient on subsequent days to try to duplicate the exact location of the cuff member on the calf to give the desired amount of suspension. With diabetic patients that often have little feeling in their feet and legs, this can be a substantial problem. Further, if the original fit needs to be modified (e.g., thicker or thinner fitting pad), the hook and loop fasteners between the cuff and brace members can be readily and infinitely adjusted. This is an important advantage as the area of the patient's leg/foot often changes (e.g., swells or atrophies) over time. Further, the present design can be prefabricated in various sizes greatly reducing the cost over current, custom walkers made from castings of the patient's foot and lower leg.

BRIEF DESCRIPTION OF THE DRAWINGS

FIG. 3 is a side elevational view of the hard, outer boot shell and the soft boot received thereon.

FIG. 4 is a perspective view of the soft boot of the suspension walker.

FIGS. 8–13 illustrate the preferred fitting method of the present invention.

FIG. 14 is a view taken along line 14—14 of FIG. 13 illustrating one of the strap members that can be wrapped around the brace members.

FIG. 15 illustrates the use of a second, removable fitting pad in the fitting method of the present invention.

FIGS. 16 and 16a also illustrate how the physician, practitioner, or therapist can choose from a variety of different, prefabricated sizes of each piece of the suspension walker to best fit the patient.

DETAILED DESCRIPTION OF THE INVENTION

Figure 1:
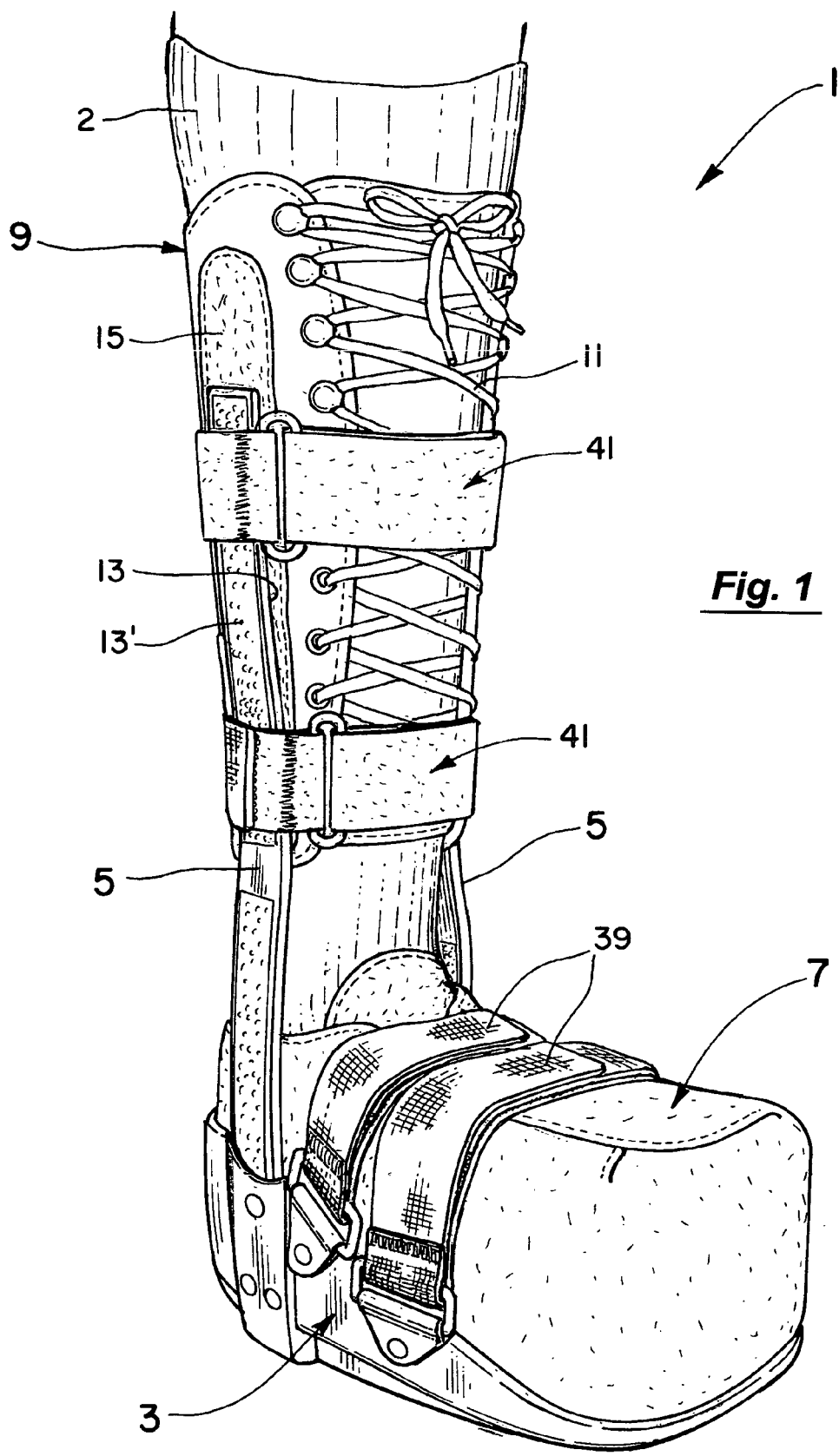
FIG. 1 is a perspective view of the suspension walker of the present invention.
Figure 2:
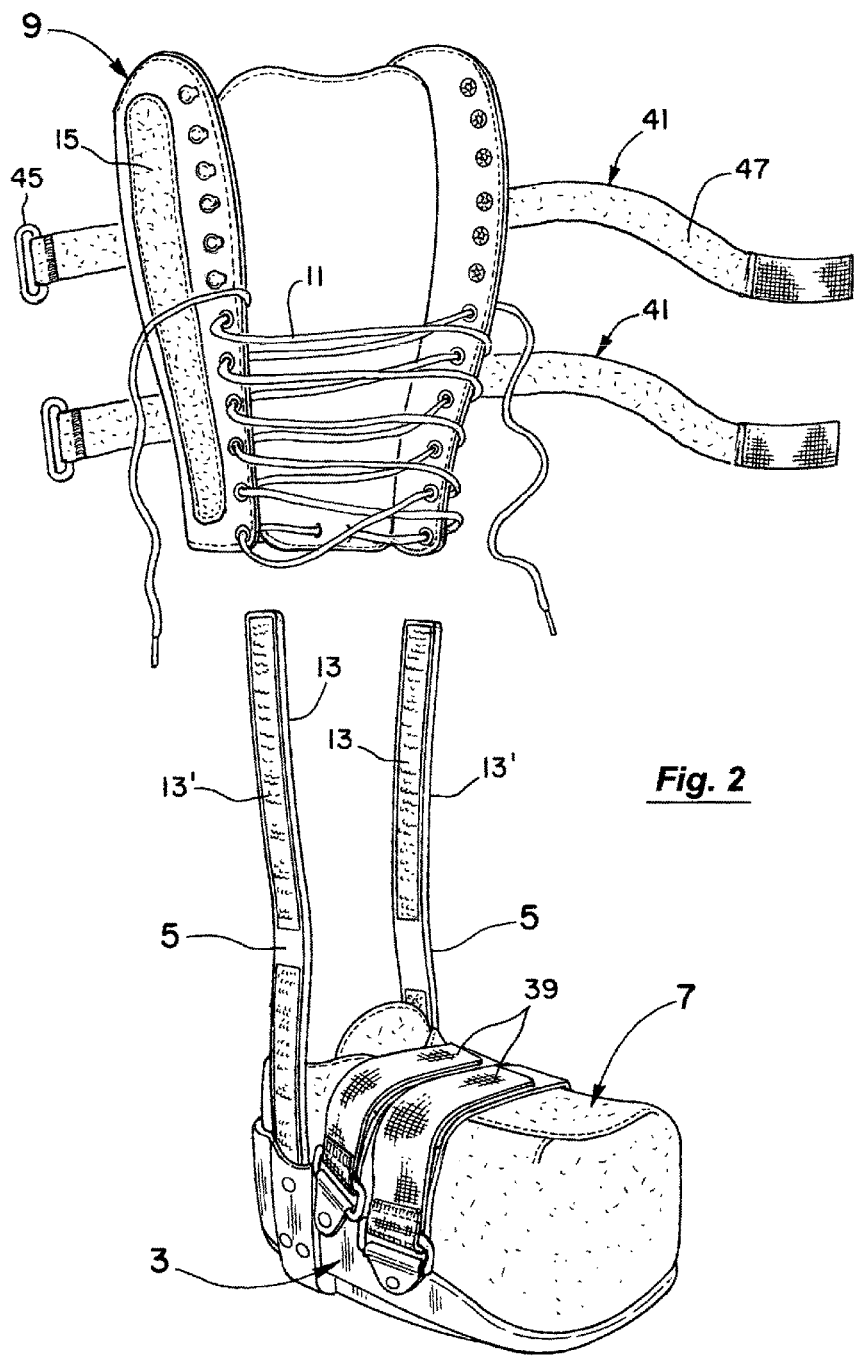
FIG. 2 is an exploded view of the suspension walker.

As best seen in FIG. 1, the suspension walker 1 of the present invention includes a hard, outer boot shell 3 with upright brace members 5 respectively extending upwardly to positions adjacent each side of the patient's calf 2. Positioned within the boot shell 3 is a soft boot 7 to receive the patient's foot. The suspension walker 1 further includes a cuff member 9 securable by laces 11 or other means to the patient's calf 2 and securable by pairs of mating hook and loop fasteners 13 and 15 (see also FIG. 2) to the upright brace members 5 of the hard, outer boot shell 3. The pairs of hook and loop fasteners 13 and 15 or other releasable attaching means as illustrated in FIGS. 1 and 2 preferably have one member (e.g., hook fastener 13 in FIG. 2) of each pair extending vertically along the inside surfaces of the brace members 5 and the other member (e.g., loop fastener 15) of each fastener pair mounted on each outer side of the cuff member 9.

Figure 5:
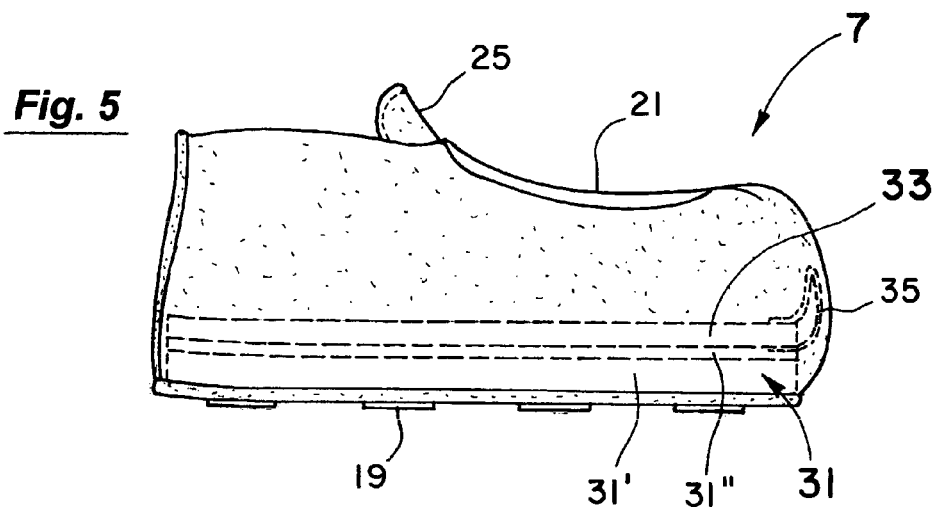
FIG. 5 is a side elevational view of the soft boot of FIG. 4.
Figure 6:
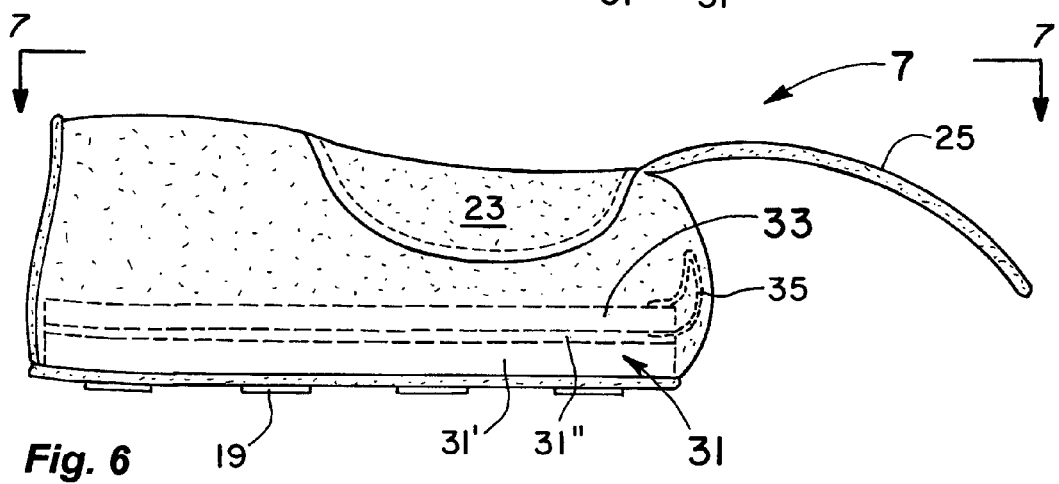
FIG. 6 is a side elevational view of the soft boot with its side flaps and tongue open to receive the patient's foot.
Figure 7:
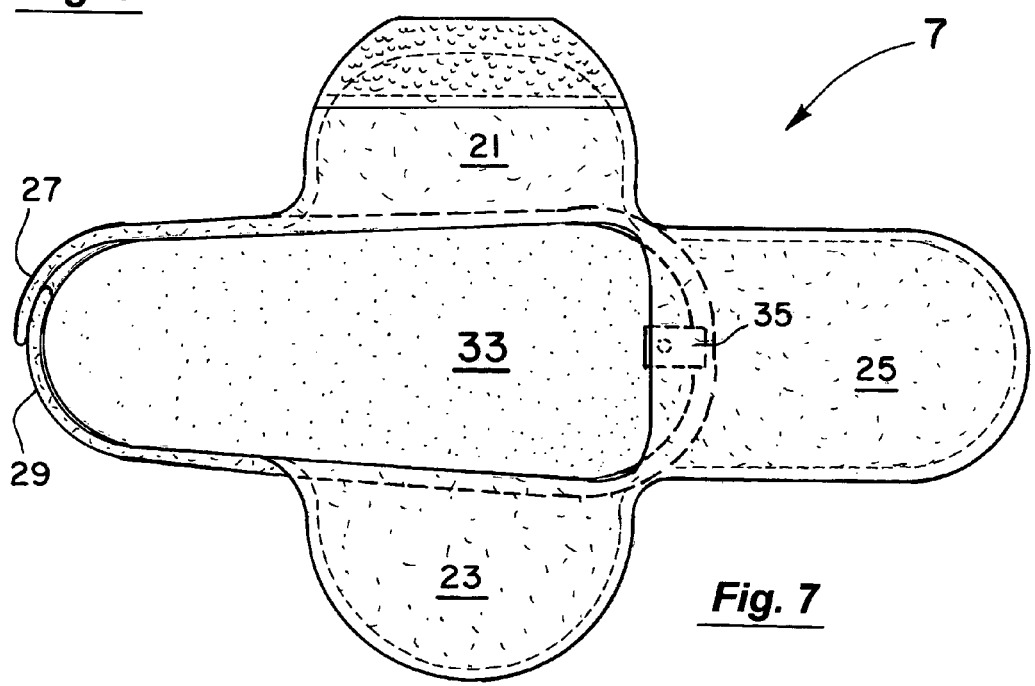
FIG. 7 is a top plan view of FIG. 6.

The hard, outer boot shell 3 and soft boot 7 as shown in FIG. 3 are removably attached to each other (e.g., by hook and loop fasteners 17 and 19). The soft boot 7 itself (see FIG. 4) has foldable side flaps 21 and 23 and a foldable tongue 25 with an adjustable heel area of overlapping and releasably securable pieces 27 and 29. The soft boot 7 as further illustrated in FIGS. 5–7 has a main pad 31 (which can be multi-layered as shown with layers 31' and 31" or a single layer) and a removable, fitting pad 33 stacked atop the main pad 31 (see FIG. 5). The fitting pad 33 preferably has a finger loop 35 on the toe end thereof and flaps 21, 23 and tongue 25 of the soft boot 7 can be opened as shown in FIGS. 6 and 7.

Figure 8:
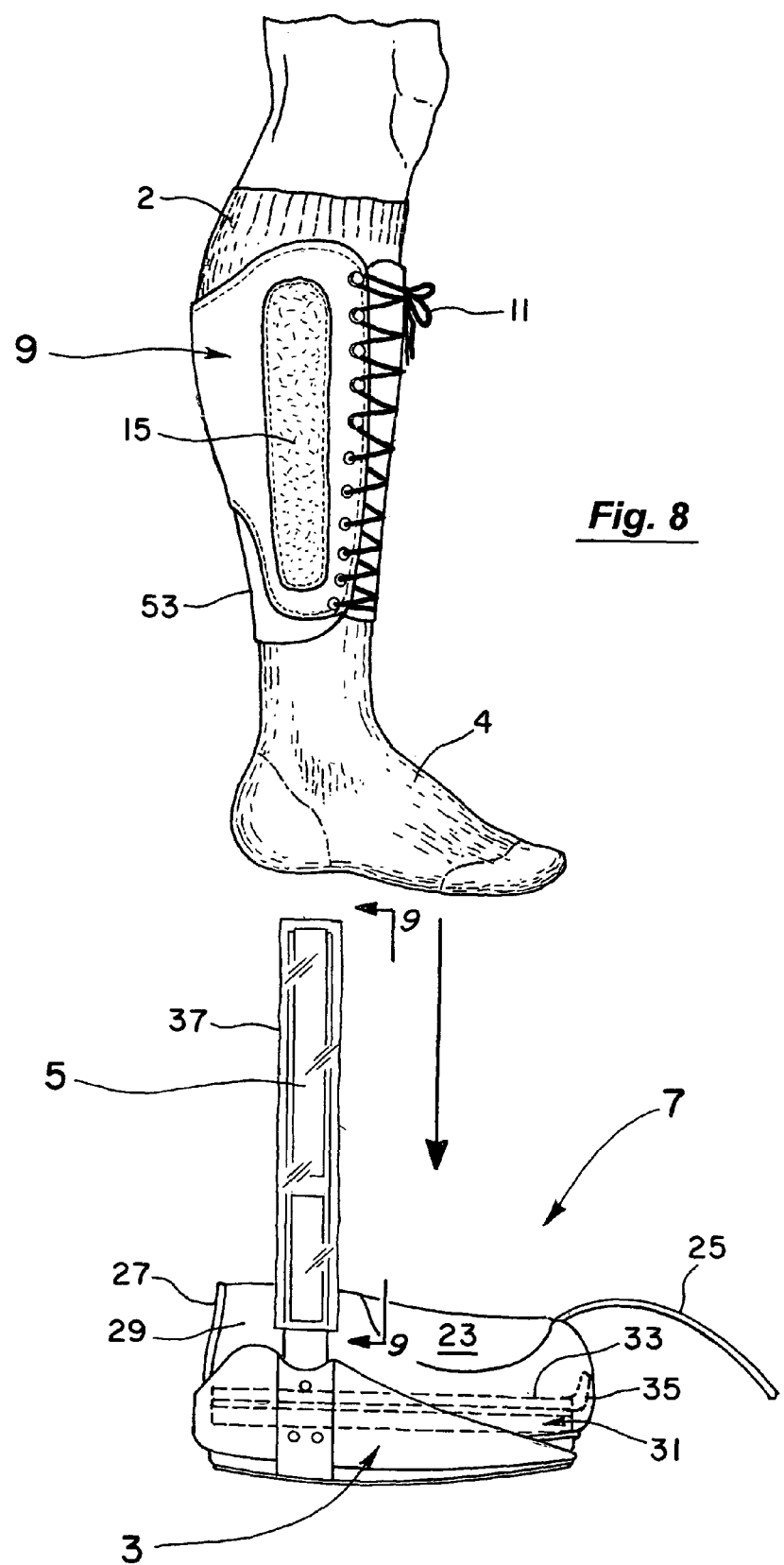

In the preferred fitting method of the present invention as shown in FIGS. 8–13, the cuff member 9 is secured by the laces 11 about the patient's socked calf 2 (see FIG. 8). With the flaps 21,23 and tongue 25 of the soft boot 7 opened (see again FIG. 8) and with tubular, plastic cover member 37 preferably over each brace member 5, the patient's foot 4 is received in the soft boot 7 (FIG. 10) atop the removable, fitting pad 33. The tubular cover members 37 (see FIGS. 8 and 9) in this regard are preferably positioned over the brace members 5 at this point to act as barriers to the engagement of the pairs of hook and loop fasteners 13 and 15 respectively on the insides of the brace members 5 and the outer sides of the cuff member 9. Consequently, the cuff member 9 can be readily slid between and past the brace members 5 from the position of FIG. 8 to the position of FIG. 10. The patient can be standing during this but is preferably sitting as in FIG. 10 to comfortably place his or her foot 2 in the soft boot 7 atop the removable, fitting pad 33 preferably with less than his or her full normal weight on the foot 4 and removable, fitting pad 33.

With the patient's calf 2 and foot 4 positioned as desired by the physician, practitioner, or therapist in FIG. 10, the fitting method then proceeds wherein the tubular cover members 37 (which to this point have acted as barriers to the engagement of the pairs of hook and loop fasteners 13 1 and 15) are removed as illustrated in FIG. 11. The pairs of mating hook and loop fasteners 13 and 15 are then secured together as also shown in FIG. 11. With the cuff member 9 secured to the vertically extending, upright brace members 5, the fitting pad 33 can now be removed (see FIG. 12) by, for example, hooking a finger in the loop 35 on the end of the fitting pad 33. The side flaps 21, 23 and tongue 25 are thereafter closed over the patient's foot 4 (see FIG. 13) with flaps 21 and 23 fastened together with hoop and loop fasteners. Straps such as 39 in FIGS. 1 and 2 if desired can be included over the closed flaps 21 and 23 to comfortably hold the patient's foot 4 in place. Further, if desired, one or more strap members 41 (see FIGS. 13 and 14) can be wrapped around and secured to the outsides of the brace members via hook and loop fasteners 13' and 43 (see FIG.

14) to aid in keeping the brace members 5 and cuff member 9 securely attached to one another. The strap members 41 in this regard can be a simple arrangement of buckle 45 and elongated strip 47 as in FIG. 14 extending about the brace members 5 and back on itself through the buckle 45. The strip 47 can then be additionally secured in place to itself by hook and loop fasteners 49 and 51 along the overlapping sides of the strip 47.

In the position of FIG. 13 following the fitting method of FIGS. 8–13, the patient's foot 4 is now at least partially suspended in the walker 1. That is, at least a portion of the patient's weight normally applied to his or her foot 4 is now transferred to and borne by the patient's calf 2 via the cuff member 9 secured to the brace members 5 of the hard, outer boot shell 3. Consequently, as the patient walks or otherwise moves around, the patient's foot 4 does not bear the weight it normally would. Depending upon how the patient is moving and any other aids he or she may be using (e.g., crutches, cane), whatever weight that would normally be applied to the foot 4 is at least partially transferred to his or her calf 2 and off of the foot 4. With the patient only using the suspension walker 1 of FIG. 13 of the present invention, the weight transferred during a normal stride with the other foot off the ground could be virtually any percentage, but preferably is in the range of at least 10%–75% and more preferably in the range of 40%–60%. In most cases, the higher the percentage of weight transferred, the better including up to 100% if the patient can otherwise safely handle it (e.g., maintain his or her balance). In most applications, the patient's heel as shown in FIG. 13 will actually be spaced or suspended (e.g., 3/16 or 1/4 inch) above the main pad 31.

To assist in fitting the patient to transfer as much as desired of his or her such normal weight to the calf 2, the removable, fitting pad 33 can be made as thick or thin as needed. Also, a second, removable fitting pad such as 33' in FIG. 15 with finger loop 35' (or any additional number of them) can be placed atop the first fitting pad 33. In this regard, it is anticipated the fitting pad 33, for example, may be 1/2 inch thick and the second fitting pad 33' on the order of 1/4 inch thick. The fitting pads 33 and 33' could then be used individually (i.e., as separate 1/2 or 1/4 inch adjustments) or together as in FIG. 15 to make an adjustment of 3/4 inch. It is noted as to the range of the relative positioning of the cuff member 9 vertically on the brace members 5 that the cuff member 9 is preferably infinitely adjustable to as precisely as possible fit the patient's needs. That is, the cuff member 9 of the preferred embodiment can be positioned at virtually any desired location vertically along each brace member 5 within the limits of the overlapping, vertically extending hook and loop fasteners 13,15. The cuff member 9 is thus infinitely, adjustably securable to each brace member 5 in any desired location vertically along a predetermined length of each brace member 5. Also, the fasteners 15 of the cuff member 9 could be portions of one, continuous member but preferably are separate strips as shown. It is additionally noted that the hook and loop fasteners mentioned throughout the description of the invention could be any other releasable securing means but hook and loop ones are preferred.

A great advantage of the fitting method of FIGS. 8–13 is that it can be done in one, simple visit with the physician, practitioner, or therapist. In contrast as discussed above, custom suspension walkers often take weeks and multiple trips to make and fit., Additionally and to the extent it is desirable to adjust the fit of FIGS. 8–13, the fitting method can be easily and quickly redone to position the cuff member 9 at virtually any number of infinite locations along the brace members 5. A further advantage of the present invention is that virtually all of the pieces (e.g., boot shell 3, soft boot 7, and cuff member 9 of FIG. 16) of the suspension walker 1 can be prefabricated in various sizes, as for example, the respective smaller sizes of boot shell 3', soft boot 7', and cuff member 9' of FIG. 16a. In this manner, the physician, practitioner, or therapist can easily select the proper size of each piece from a variety of them on hand. The patient can then be properly fitted and begin using the suspension walker 1 immediately to relieve weight from the damaged foot and to begin the healing process. No waiting or delay to receive the walker is involved. With diabetic and other patients as discussed above, this is extremely important.

Figure 16:
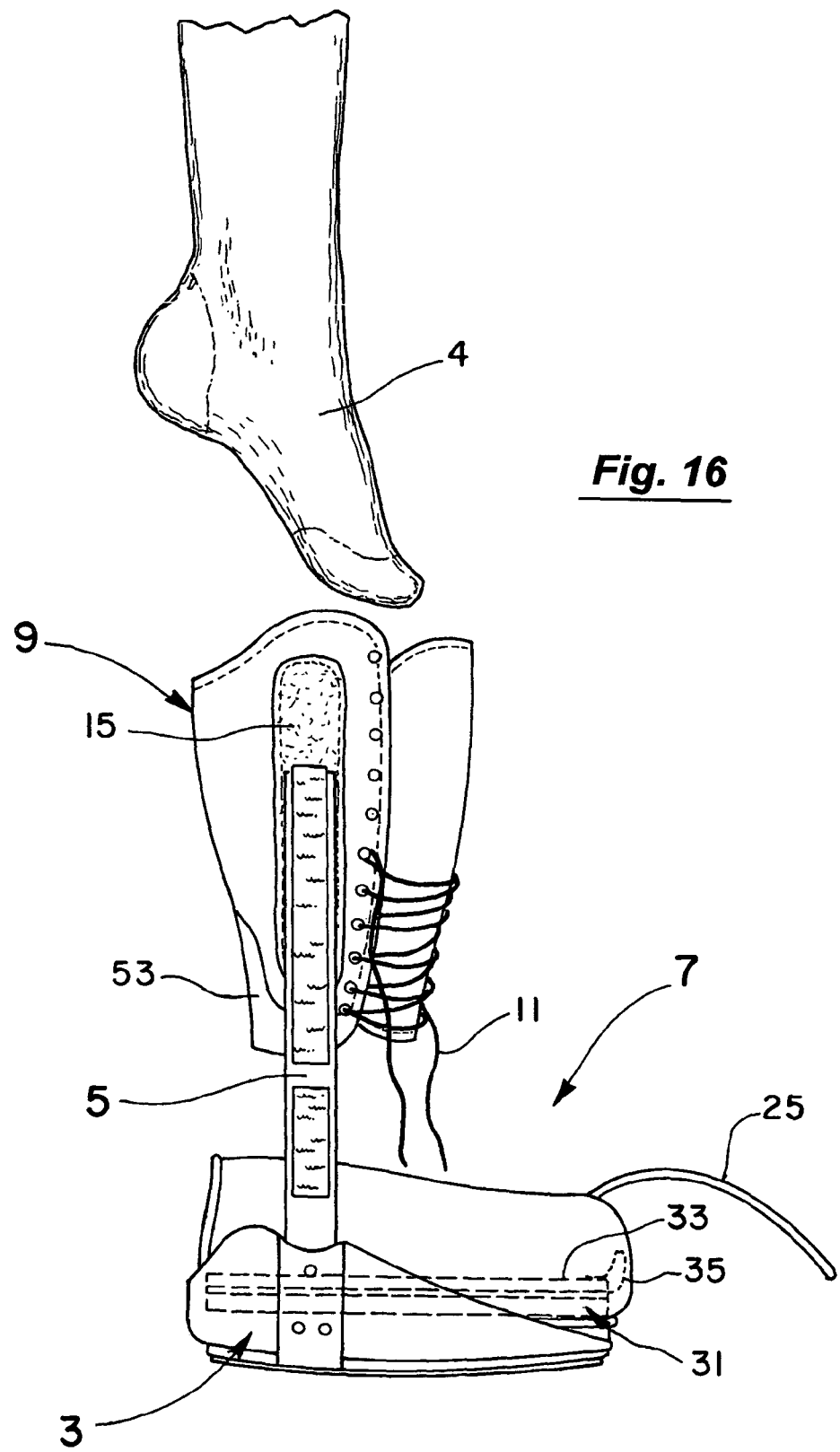
FIGS. 16 and 17 illustrate the manner in which the patient can subsequently put on the suspension walker to duplicate the original fitting position set by the physician, practitioner, or therapist.
Figure 16A:
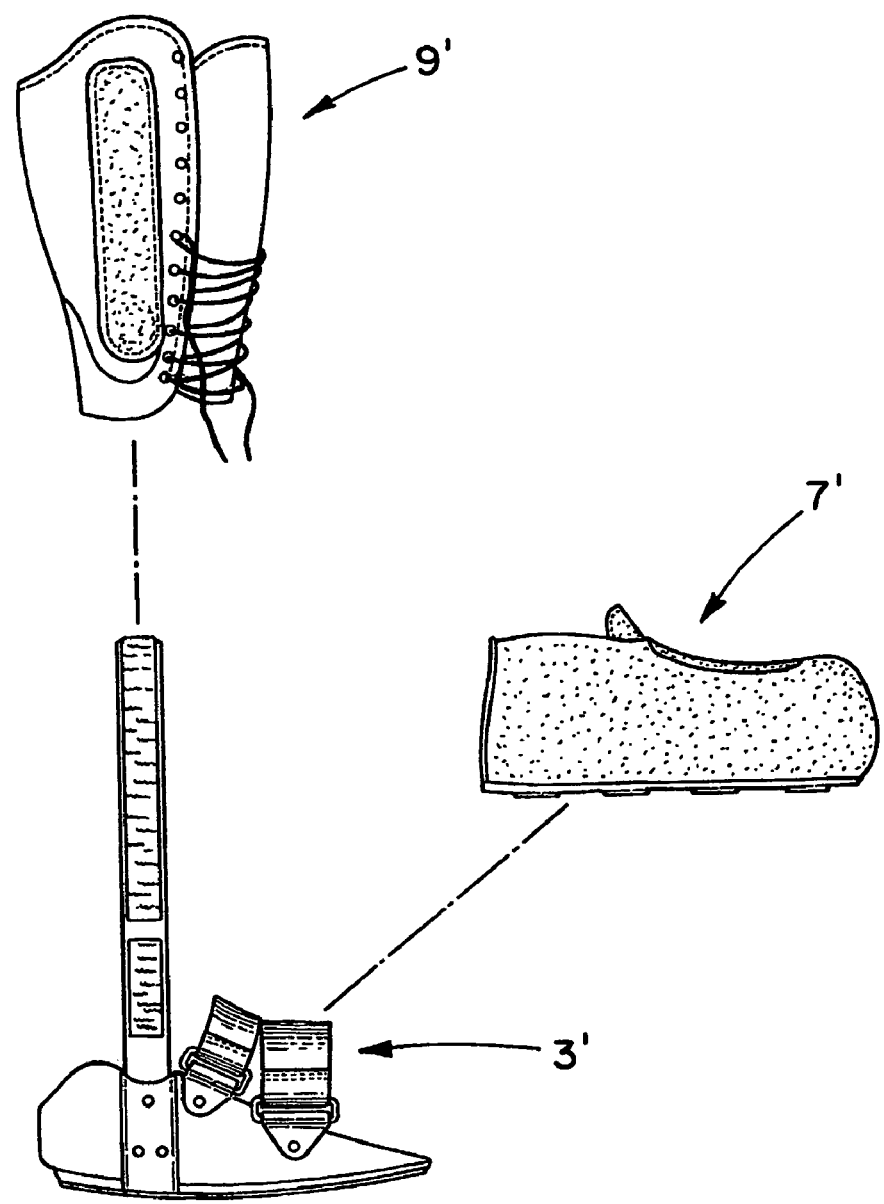
Figure 17:
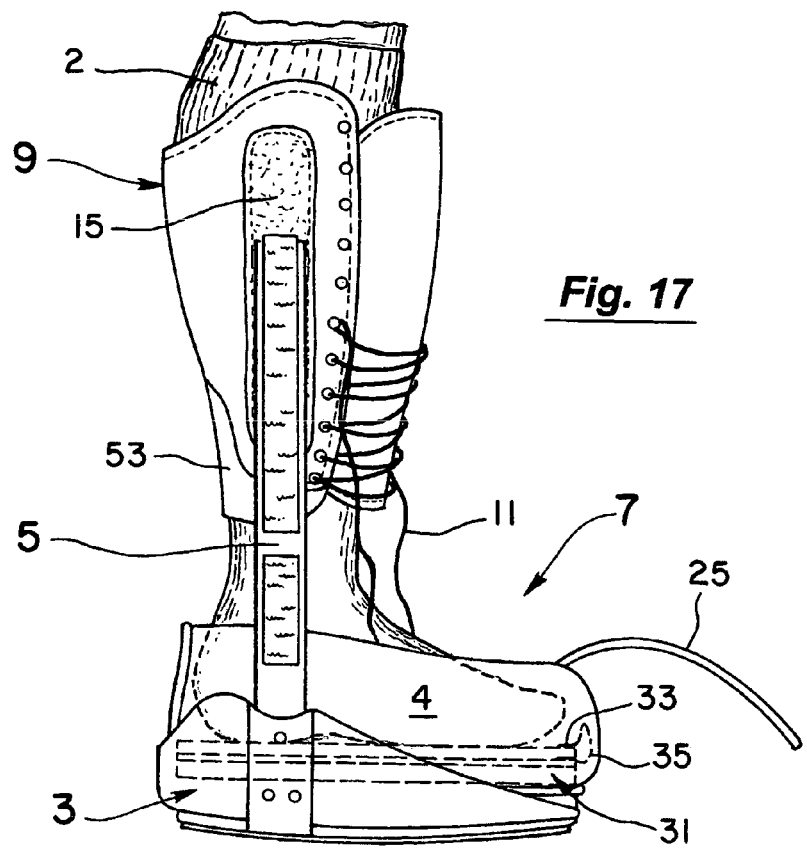
Figure 18:
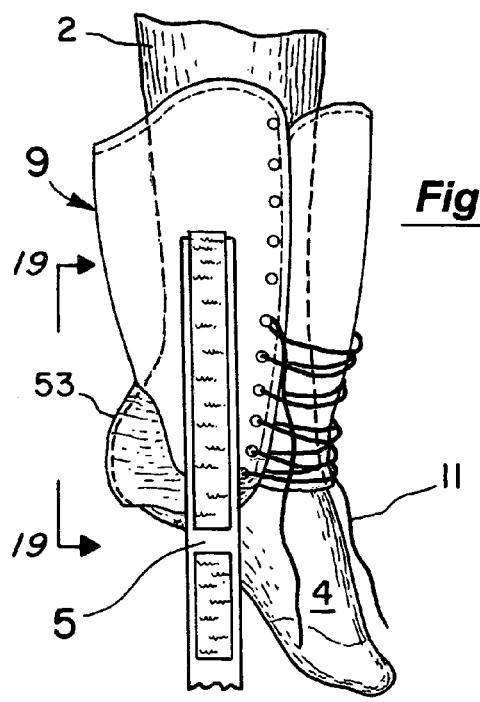
FIGS. 18 and 19 illustrate the elastic, heel section of the cuff member to aid the patient in putting on and taking off the cuff member.
Figure 19:
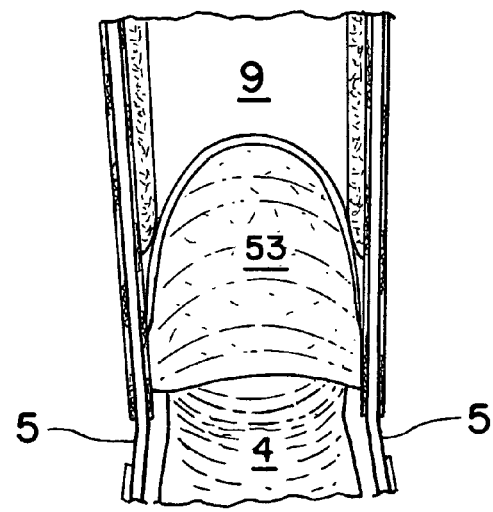

Once the initial, fitting process is accomplished as in FIGS. 8–13, the same fit and unweighting of FIG. 13 can be subsequently duplicated by the patient by himself or herself on later uses of the suspension walker 1 of the present invention. More specifically and as illustrated in FIGS. 16 and 17, the patient in subsequent uses need only place his or her foot 4 into the cuff member 9 (FIG. 16) and atop the removable, fitting pad 33 of FIG. 17. The removable, fitting pad 33 in this regard has been replaced atop the multi-layered main pad 31 after the prior use of the suspension walker 1. In the position of FIG. 17, the laces 11 or other securing means can then be tightened to secure the cuff member 9 to the calf 2. The steps of FIGS. 12 and 13 can thereafter be repeated and the suspension walker 1 is again properly fitted in the identical position originally set by the physician, practitioner, or therapist. As an aid to sliding the patient's foot 4 into and out of the cuff member 9, an elastic, expandable heel section 53 is provided at the lower rear area of the cuff member 9 (see FIGS. 18 and 19). In use as best seen in FIG. 18, the heel section 53 expands as the patient would pull up on the cuff member 9 while inserting his or her foot 4. Conversely, in removing the cuff member 9, the heel section 53 expands as the patient would push down on the cuff member 9 while withdrawing his or her foot 4.

As mentioned above and although hook and loop fasteners have primarily been used throughout the description of the present invention to releasably secure or attach the various members together, other releasable securing means (e.g., buckles, straps, snaps, buttons) could be used if desired. Also, the suspension walker 1 preferably uses laces 11 to removably secure the cuff member 9 to the patient's calf 2 although other securing means (e.g., hook and loop fasteners, buckles, snaps) could be used. Laces in this use are preferred as they create a more evenly distributed pressure over the calf area.

Figure 20:
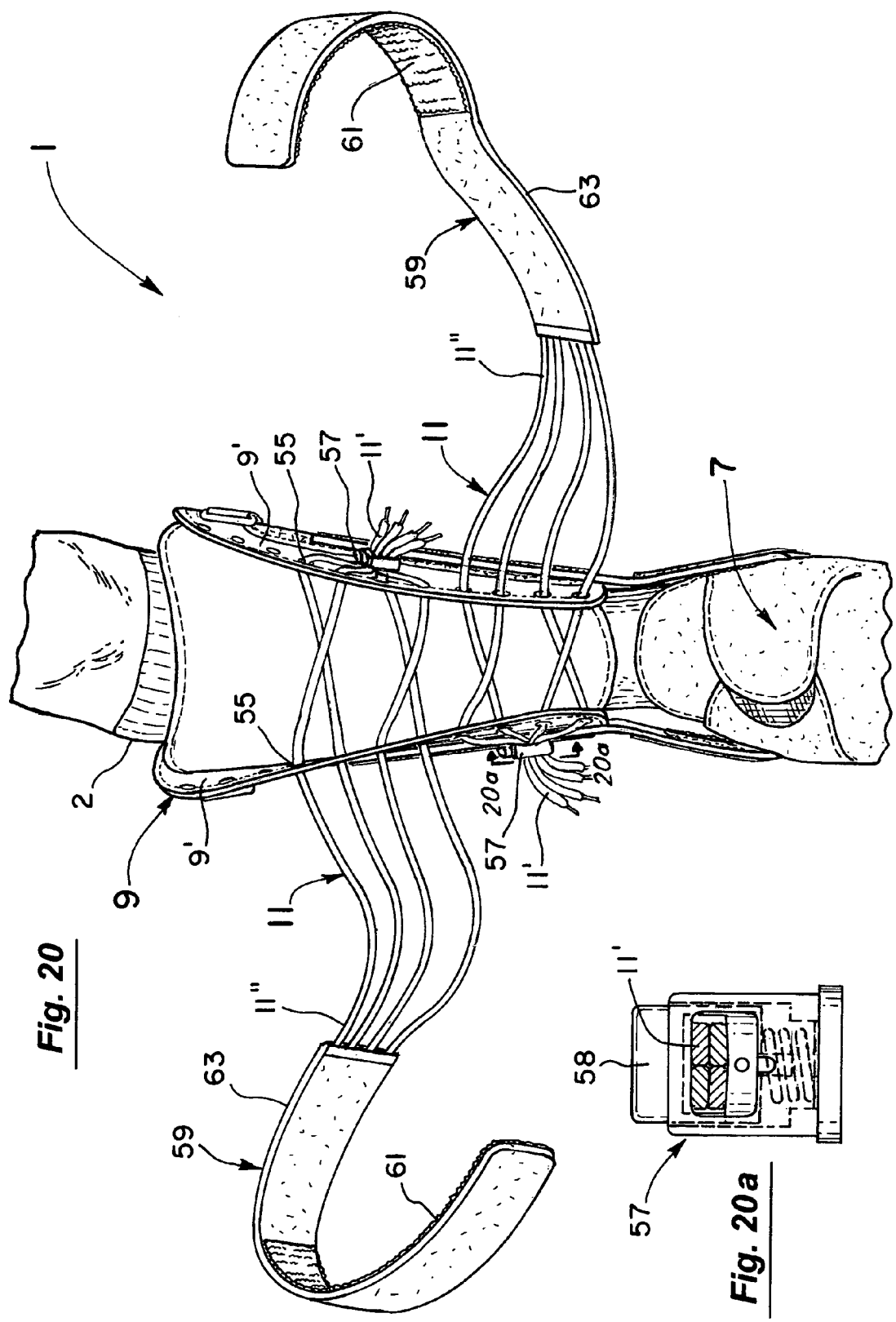
FIGS. 20–22 including FIG. 20a illustrate an alternate manner of releasably securing the cuff member to the patient's calf combing the benefit of the even pressure of laces with the convenience of a quick attachment arrangement such as hook and loop fasteners.
Figure 21:
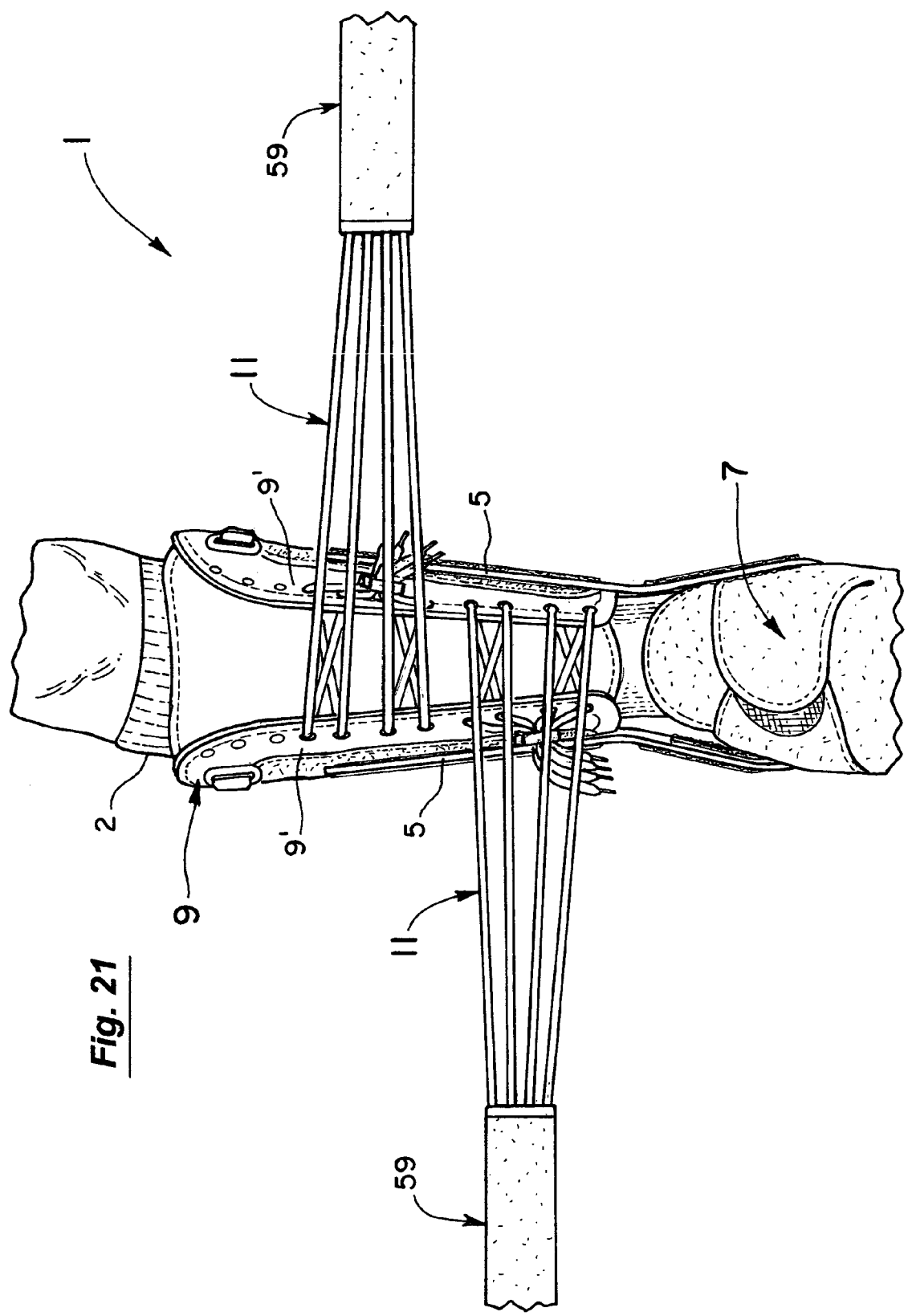
Figure 22:
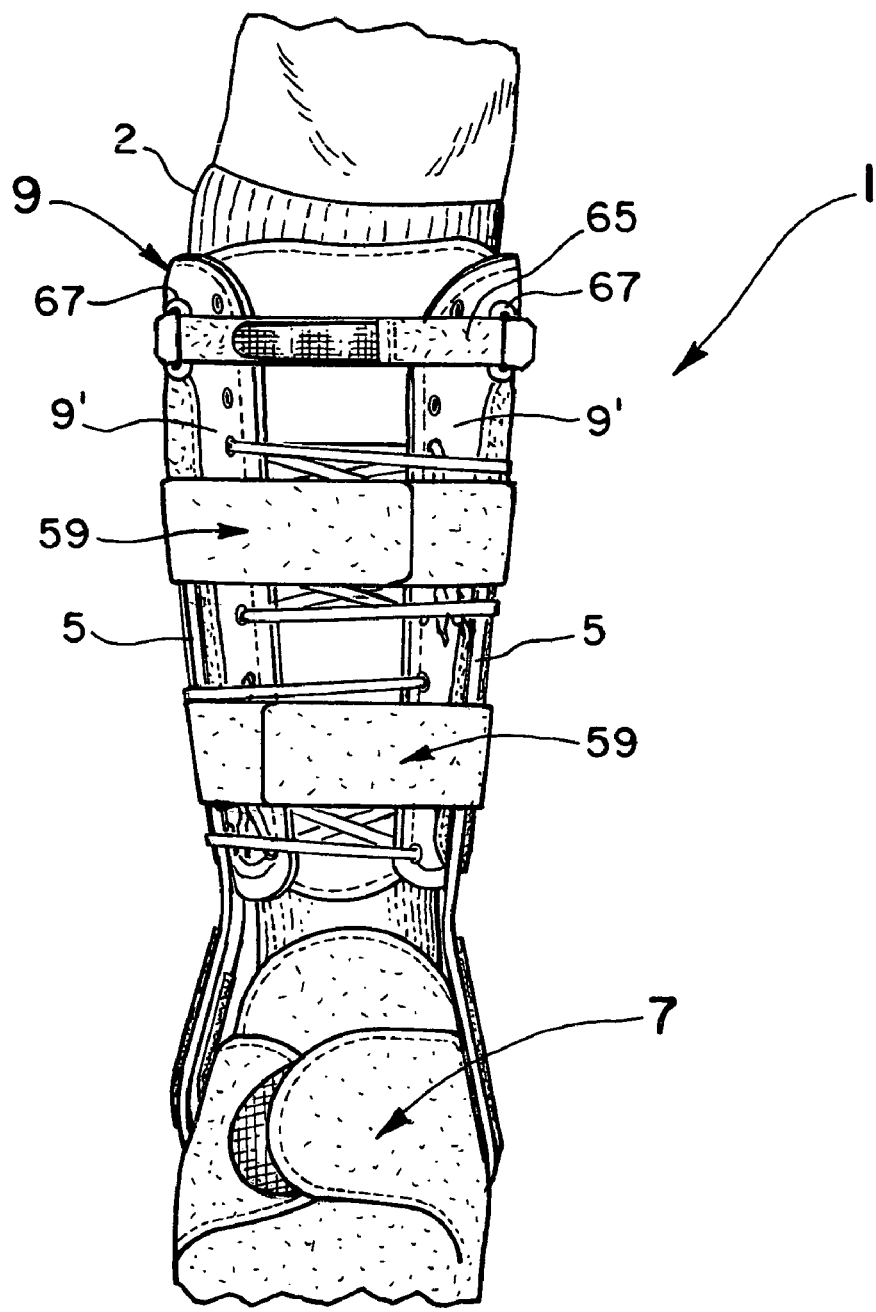

In this last regard, FIGS. 20–22 illustrate an alternate way of releasably securing the cuff member 9 to the patient's calf 2. This alternative manner combines the benefit of laces (i.e., even pressure) with the convenience of a quick attachment arrangement (e.g., hook and loop fasteners). More specifically as shown in FIG. 20, each set of upper and lower laces 11 is passed through eyelets 55 on each side piece 9' of the cuff member 9. The free ends 11' of the laces 11 are then gathered and releasably secured in place adjacent one of the side pieces 9' by respective clamp members 57 (see FIG. 20a). The clamp members 57 can be free standing as in FIGS. 20 and 20a or mounted to the side piece 9' if desired. The two sets of laces 11 as shown in FIG. 20 are preferably provided in a mirror image manner. In use, the strips 59 to which the other ends 11" of the laces 11 are attached (e.g., sewn) are thereafter crossed over (see FIG. 21) to the respective other side 9' of the cuff member 9 to pull the respective sets of laces 11 tight. The strips 59 are subsequently wrapped around the brace members 5 and cuff member 9 and around on themselves as in FIG. 22. The strips 59 (see FIG. 20) like straps 41 in FIGS. 13 and 14 have mating hook and loop fasteners 61 and 63 on opposite sides of each strip 59 and can thereby be secured in place (FIG. 22) to each other and to the brace members 5. An additional, top strip 65 between buckles 67 as shown in FIG. 22 can also be provided if desired and similarly secured in place by hook and loop fasteners.

In the alternative manner of FIGS. 20–22, the cuff member 9 can be easily and quickly put on and taken off the patient's calf 2. Additionally if needed, the effective lengths of the laces 11 of each set can be individually or collectively shortened by releasing the clamp members 57 (e.g., depressing member 58 in FIG. 20a) and pulling the lace ends 11' away from the cuff member 9 in FIG. 20. Similarly, the effective lengths can be lengthened by pulling the other lace ends 11" or attached strips 59 away from the cuff member 9 with the clamp members 57 released. As indicated above and with the alternate design of FIGS. 20–22, the benefit of laces (i.e., even pressure) with the convenience of a quick attachment method (e.g., hook and loop fasteners) is achieved. Although specifically shown in use to releasably secure the cuff member 9 about the patient's calf 2, the alternate design of FIGS. 20–22 could be used to removably secure any member about any part of the patient's body or about any object.

While several embodiments of the present invention have been shown and described in detail, it to be understood that various changes and modifications could be made without departing from the scope of the invention.

I claim:

1. A method for fitting a suspension walker on a patient to transfer at least a portion of the patient's weight normally applied to the patient's foot to the patient's calf to thereby at least partially suspend the patient's foot in the walker, said method including the steps of:
   (a) providing a hard, outer boot shell with upright brace members on each side respectively extending upwardly to positions adjacent each side of the patient's calf,
   (b) providing a soft boot on said hard, outer boot shell to receive the patient's foot with said soft boot having at least a main pad and a removable, fitting pad atop said main pad,
   (c) providing a cuff member securable about the patient's calf and securable to said brace members,
   (d) securing said cuff member about the patient's calf,
   (e) placing the patient's foot in the soft boot atop said removable, fitting pad and said main pad,
   (f) securing said cuff member to each brace member at respective locations therealong, and
   (g) removing said fitting pad wherein said portion of the patient's weight normally applied to the foot is transferred to and borne by the patient's calf via the cuff member secured to said brace members of the hard, outer boot shell to at least partially suspend the patient's foot in the walker.

2. The fitting method of claim 1 wherein step (f) includes the further limitation of releasably securing said cuff member to said brace members.

3. The fitting method of claim 1 wherein step (f) includes the further limitation of releasably securing said cuff member to said brace members with pairs of mating hook and loop fasteners respectively mounted between said cuff member and said brace members.

4. The fitting method of claim 3 further including the limitation of extending one of each pair of said hook and loop fasteners vertically along each brace member and wherein the fitting method further includes the limitation prior to step (f) of providing a removable barrier between the respective mating pairs of hook and loop fasteners of each brace member and the cuff member and further includes the limitation between steps (e) and (f) of removing said barriers.

5. The fitting method of claim 4 further including the limitation of providing said barriers by sliding respective tubular cover members over the respective brace members.

6. The fitting method of claim 1 further including the step of vertically adjusting the locations of the securement of the cuff member to the brace members.

7. The fitting method of claim 1 further including the step of vertically and infinitely adjusting the locations of the securement of the cuff member to the brace members.

8. The fitting method of claim 1 wherein step (b) includes the further limitation of providing a second, removable fitting pad atop the first mentioned fitting pad and the main pad.

9. The fitting method of claim 1 wherein step (b) includes the further limitation of providing a second, removable fitting pad atop the first mentioned fitting pad and the main pad and step (g) includes the further limitation of removing said second fitting pad.

10. The fitting method of claim 1 wherein step (d) includes the further limitation of securing said cuff member about the calf of the patient with laces.

11. The fitting method of claim 1 further including the step of:
   (h) wrapping at least one strap member about said brace members secured to the cuff member.

12. The fitting method of claim 11 further including the limitation in step (h) of securing said one strap member in place about said brace members with mating hook and loop fasteners.

13. The fitting method of claim 11 further including the limitation in step (h) of securing said one strap member to said brace members with hook and loop fasteners.

14. The fitting method of claim 13 further including the limitation of extending one of the hook and loop fasteners vertically along each brace member.

15. The fitting method of claim 1 further including the limitation of providing an elastic, expandable heel section on the lower rear area of the cuff member.

16. The fitting method of claim 1 further including the limitation of transferring at least about 10% to about 75% of the patient's normal weight on the foot to the patient's calf via the cuff member secured to said brace members.

17. The fitting method of claim 1 further including the limitation of transferring about 40% to about 60% of the patient's normal weight on the foot to the patient's calf via the cuff member secured to said brace members.

18. The fitting method of claim 1 further including the limitation of selecting at least one of the outer boot shell, soft boot, and cuff member from at least two different, prefabricated sizes.

19. The fitting method of claim 1 wherein each of the outer boot shell, soft boot, and cuff member is selected from at least two different, prefabricated sizes.

20. The fitting method of claim 1 further including the limitations of providing said cuff member with two side pieces, attaching a plurality of laces adjacent one end of each lace to one of said side pieces, passing said laces through eyelets on the other side piece, securing the other end of each lace to a strip, and wrapping said strip about said brace members and cuff member to draw said laces tight.

21. A method for fitting a suspension walker on a patient to transfer at least a portion of the patient's weight normally applied to the patient's foot to the patient's calf to thereby at least partially suspend the patient's foot in the walker, said method including the steps of:
  (a) providing a hard, outer boot shell with upright brace members on each side respectively extending upwardly to positions adjacent each side of the patient's calf,
  (b) providing a soft boot on said hard, outer boot shell to receive the patient's foot with said soft boot having at least a main pad and a removable, fitting pad atop said main pad,
  (c) providing a cuff member secured to said brace members and securable about the patient's calf,
  (d) placing the patient's foot in the soft boot atop said removable, fitting pad and said main pad,
  (e) securing said cuff member about the patient's calf, and
  (f) removing said fitting pad wherein said portion of the patient's weight normally applied to the foot is transferred to and borne by the patient's calf via the cuff member secured to said brace members of the hard, outer boot shell to at least partially suspend the patient's foot in the walker.

22. The fitting method of claim 21 wherein step (b) includes the further limitation of providing a second, removable fitting pad atop the first mentioned fitting pad and the main pad.

23. The fitting method of claim 21 wherein step (b) includes the further limitation of providing a second, removable fitting pad atop the first mentioned fitting pad and the main pad and step (f) includes the further limitation of removing said second fitting pad.

24. The fitting method of claim 21 wherein step (e) includes the further limitation of securing said cuff member about the calf of the patient with laces.

25. The fitting method of claim 21 further including the step of:
  (g) wrapping at least one strap member about said brace members secured to the cuff member.

26. The fitting method of claim 25 further including the limitation in step (g) of securing said one strap member in place about said brace members with mating hook and loop fasteners.

27. The fitting method of claim 25 further including the limitation in step (g) of securing said one strap member to said brace members with hook and loop fasteners.

28. The fitting method of claim 21 further including the limitation of providing an elastic, expandable heel section on the lower rear area of the cuff member.

29. The fitting method of claim 21 further including the limitation of transferring at least about 10% to about 75% of the patient's normal weight on the foot to the patient's calf via the cuff member secured to said brace members.

30. The fitting method of claim 21 further including the limitation of transferring about 40% to about 60% of the patient's normal weight on the foot to the patient's calf via the cuff member secured to said brace members.

31. The fitting method of claim 21 further including the limitations of providing said cuff member with two side pieces, attaching a plurality of laces adjacent one end of each lace to one of said side pieces, passing said laces through eyelets on the other side piece, securing the other end of each lace to a strip, and wrapping said strip about said brace members and cuff member to draw said laces tight.

32. A suspension walker to transfer at least a portion of a patient's weight normally applied to the patient's foot to the patient's calf to thereby at least partially suspend the patient's foot in the walker, said suspension walker including:
  a hard, outer boot shell with upright brace members on each side respectively extending upwardly to positions adjacent each side of the patient's calf,
  a soft boot on said hard, outer boot shell to receive the patient's foot with said soft boot having at least a main pad and a removable, fitting pad atop said main pad, and
  a cuff member securable about the patient's calf and securable to said brace members wherein the patient's foot can be placed in the soft boot atop said removable fitting pad and main pad, said cuff member can be secured to said brace members at respective locations therealong, and said fitting pad can be removed wherein said portion of the patient's weight normally applied to the foot can be transferred to and borne by the patient's calf via the cuff member secured to said brace members of the hard, outer boot shell to at least partially suspend the patient's foot in the walker.

33. The suspension walker of claim 32 wherein said cuff member is releasably securable to said brace members.

34. The suspension walker of claim 32 wherein said cuff member is infinitely, adjustably securable to said brace members vertically along a predetermined length of each brace member.

35. The suspension walker of claim 32 wherein said cuff member is releasably securable to said brace members by pairs of mating hook and loop fasteners respectively mounted between said cuff member and said brace members.

36. The suspension walker of claim 35 wherein one of each pair of mating hook and loop fasteners is mounted vertically along each brace member and the respective other of each pair of mating hook and loop fasteners is mounted to the cuff member.

37. The suspension walker of claim 32 wherein said cuff member is releasably securable about the calf of the patient by laces.

38. The suspension walker of claim 32 further including at least a second, removable fitting pad positional atop the first mentioned fitting pad and the main pad.

39. The suspension walker of claim 32 further including at least one strap member securable about said brace members.

40. The suspension walker of claim 32 further including an elastic, expandable heel section on the lower rear area of the cuff member.

41. The suspension walker of claim 32 wherein said cuff member has two side pieces with a plurality of laces adjacent one end of each lace attached to one of said side pieces, said laces passing through eyelets on the other side piece with the other end of each lace secured to a strip wherein said strip can be wrapped about said brace members and cuff member to draw said laces tight.

42. A suspension walker to transfer at least a portion of a patient's weight normally applied to the patient's foot to the patient's calf to thereby at least partially suspend the patient's foot in the walker, said suspension walker including:
  a hard, outer boot shell with upright brace members on each side respectively extending upwardly to positions adjacent each side of the patient's calf,
  a soft boot on said hard, outer boot shell to receive the patient's foot with said soft boot having at least a main pad, and
  a cuff member securable about the patient's calf and infinitely, adjustably securable to said brace members vertically along a predetermined length of each brace member, and an elastic, expandable heel section on the lower rear area of the cuff member.

43. A suspension walker to transfer at least a portion of a patient's weight normally applied to the patient's foot to the patient's calf to thereby at least partially suspend the patient's foot in the walker, said suspension walker including:

a hard, outer boot shell with upright brace members on each side respectively extending upwardly to positions adjacent each side of the patient's calf, a soft boot on said hard, outer boot shell to receive the patient's foot with said soft boot having at least a main pad, and a cuff member securable about the patient's calf and infinitely, adjustably securable to said brace members vertically along a predetermined length of each brace member wherein said cuff member has two side pieces with a plurality of laces adjacent one end of each lace attached to one of said side pieces, said laces passing through eyelets on the other side piece with the other end of each lace secured to a strip wherein said strip can be wrapped about said brace members and cuff member to draw said laces tight.

* * * * *